US005576291A

United States Patent [19]

Curtis et al.

[11] Patent Number: 5,576,291
[45] Date of Patent: Nov. 19, 1996

[54] ACTIVATED FACTOR VIII AS A THERAPEUTIC AGENT AND METHOD OF TREATING FACTOR VIII DEFICIENCY

[75] Inventors: Joseph E. Curtis, Glendora; Sam L. Helgerson, Pasadena, both of Calif.; Roger L. Lundblad, Chapel Hill, N.C.; Shu-Len Liu, Cerritos, Calif.

[73] Assignee: Baxter International Inc., Deerfield, Ill.

[21] Appl. No.: 120,894

[22] Filed: Sep. 13, 1993

[51] Int. Cl.$^6$ .......................... A61K 38/36; A61K 38/37; C07K 14/745; C07K 14/755
[52] U.S. Cl. .............................. 514/12; 514/21; 514/802; 514/834; 530/381; 530/383; 530/830
[58] Field of Search ...................................... 530/383, 380, 530/381, 829, 830; 514/12, 21, 802, 834

[56] References Cited

U.S. PATENT DOCUMENTS

| | | |
|---|---|---|
| 4,386,068 | 5/1983 | Mitra et al. . |
| 4,387,092 | 6/1983 | Liautaud et al. .......................... 530/383 |
| 4,404,131 | 9/1983 | Schwarz et al. ........................ 530/383 |
| 4,508,709 | 4/1985 | Amphlett et al. ......................... 530/383 |
| 4,649,132 | 3/1987 | Zimmerman et al. ....................... 514/12 |
| 4,757,006 | 7/1988 | Toole, Jr. et al. ......................... 435/69.6 |
| 4,758,657 | 7/1988 | Farb et al. ............................... 530/383 |
| 4,769,336 | 9/1988 | Zimmerman et al. .................... 436/518 |
| 4,795,806 | 1/1989 | Brown et al. ............................. 530/383 |
| 4,831,119 | 5/1989 | Nordfang et al. ........................ 530/383 |
| 4,857,635 | 8/1989 | Zimmerman et al. ................... 530/383 |
| 4,868,112 | 9/1989 | Toole, Jr. ..................................... 514/8 |
| 4,877,614 | 10/1989 | Andersson et al. . |
| 4,965,199 | 10/1990 | Capon et al. ............................ 435/69.6 |
| 4,980,456 | 12/1990 | Scandella et al. ........................ 530/383 |
| 4,981,951 | 1/1991 | Tsay ......................................... 530/383 |
| 5,101,016 | 3/1992 | Zimmerman et al. ................... 530/383 |
| 5,149,687 | 9/1992 | Scandella et al. ....................... 435/69.6 |
| 5,171,844 | 12/1992 | van Ooyen et al. ...................... 530/383 |

FOREIGN PATENT DOCUMENTS

| | | |
|---|---|---|
| 0123945A1 | 7/1984 | European Pat. Off. . |
| 182372 | 5/1986 | European Pat. Off. . |
| WO88/08035 | 10/1988 | WIPO . |

OTHER PUBLICATIONS

Pittman et al. A2 Domain of Human Recombinant–Derived Factor VIII etc. Blood, vol. 79, No. 2, pp. 389–397, Jan. 15, 1992.
Scandella et al. Human Factor VIII Inhibitors: Further Epitope etc., Thrombosis Haemostasis, vol. 58, Issue 1, p. 520, 1987.
Curtis et al. Characterization of a Stable Preparation of Thrombin—etc., American Society of Hematology Meeting, Anaheim, California, Dec. 8, 1992.
Tuddenham et al. The Properties of Factor VIII Coagulant Activity etc., The C. V. Mosby Company, J. Lab. Clin. Med. vol. 93, No. 1, pp. 40–53, Jan. 1979.
Weinstein et al. Analysis of Factor VIII Coagulant Antigen etc., Proc. Natl. Acad. Sci. USA, vol. 78, No. 8, pp. 5137–5141, Aug. 1981.
Vehar et al. Structure of Human Factor VIII Nature vol. 312, pp. 337–342, Nov. 22, 1984.
Fulcher et al. Localization of Human Factor VIII Inhibitor etc. Proc. Natl. Acad. Sci. USA, vol. 82, pp. 7728–7732, Nov. 1985.
Brinkhous et al. Purified Human Factor VIII Procoagulant Protein etc. Proc. Natl. Acad. Sci. USA, vol. 82, pp. 8752–8756, Dec. 1985.
Eaton et al. Construction and Characterization of an Active Factor etc. Biochemistry, vol. 25, No. 26, pp. 8343–8346, Dec. 30, 1986.
Eaton et al. Characterization of Recombinant Human Factor VIII The J. of Biological Chemistry, vol. 262, No. 7, pp. 2385–3290, Mar. 5, 1987.
Nordfang et al. FVIII Subunits: Purification and Antigenic Properties Thrombosis and Haemostasis 58 (4) 1043–1048, 1987.
Scandella et al. Epitope Mapping of Human Factor VIII Inhibitor etc. Proc. Natl. Acad. Sci. USA, vol. 85, pp. 6152–6156, Aug. 1988.
Lollar et al. Subunit Structure of Thrombin–Activated Porcine etc. Biochemistry 1989, 28, 666–674.
White et al. Factor VIII Gene and Hemophilia A Blood Reviews (1989) 3, 180–191; Blood vol. 73, No. 1, pp. 1–12, Jan. 1989.
Bihoreau et al. Isolation and Characterization of Different etc. Eur. J. Biochem. 185, 111–118 (1989) Feb.
Scandella et al. Localization of Epitopes for Human Factor VIII etc. Blood, vol. 74, No. 5, Oct. 1989, pp. 1618–1626.
Tuddenham, Factor VIII and Haemophilia A Bailliere's Clinical Haematology, vol. 2, No. 4, Oct. 1989, pp. 849–877.
Kaufman, Genetic Engineering of Factor VIII Nature vol. 342, 9 Nov. 1989, pp. 207–208.
Nordfang, Coagulation Factor VIII European J. of Haematology, Supplementum No. 49, vol. 43, 1989.
Lollar et al. PH–Dependent Denaturation of Thrombin–Activated etc. The J. of Biological Chemistry, vol. 265, No. 3, pp. 1688–1692, Jan. 25, 1990.
Foster et al. Synthetic Factor VIII Peptides With Amino Acid etc. Blood, vol. 75, No. 10, pp. 1999–2004, May 15, 1990.
Kemball–Cook et al. Factor VIII Heavy Chain Polypeptides in Plasma etc. British Journal of Haematology, 1990, 76, 80–87.
Foster et al. A Synthetic Factor VIII Peptide of Eight Amino Acid etc. Thrombosis and Haemostasis, 63 (3) 403–406 (1990).

(List continued on next page.)

*Primary Examiner*—Mindy Fleisher
*Assistant Examiner*—Nancy J. Degen
*Attorney, Agent, or Firm*—Janice Guthrie; Robert E. Hartenberger

[57] ABSTRACT

Stabilized and activated Factor VIII is used as a therapeutic agent to treat patients with a Factor VIII deficiency. This includes hemophilia A patients as well as patients with Factor VIII inhibitors which block the hemostatic activity of Factor VIII. The stabilized and activated Factor VIII is also prepared in a therapeutic composition with a therapeutically acceptable adjuvant.

20 Claims, No Drawings

OTHER PUBLICATIONS

Krishnan et al. Thrombin Cleavage Analysis of a Novel etc. Eur. J. Biochem. 195, pp. 637–644 (Received 1990) Feb. 1991.

Ingerslev et al. Clinical Experience with Hemofil M in a Hemophilia etc. Ann. Hematol (1991) 63:52–154.

Fay et al. Human Factor VIIIA Subunit Structure Reconstitution etc. The J. of Biological Chemistry vol. 266, No. 14, pp. 8957–8962, May 15, 1991.

Lollar et al. Structural Basis for the Decreased Procoagulant etc. The J. of Biological Chemistry vol. 266, No. 19, pp. 12481–12486, Jul. 5, 1991.

Fay et al. Characterization of the Interaction Between the A2 Subunit etc. The J. of Biological Chemistry vol. 267, No. 19, pp. 13246–13250, Jul. 5, 1992.

Foster et al. Factor VIII Structure and Function Blood Reviews (1989) 3, 180–191; 1989 Longman Group UK Ltd.

Curtis J. E., et al. Structural Studies of Human Factor VIII etc.

The Journal of Biological Chem. vol. 269, No. 8, 25 Feb. 1994, Baltimore USA, pp. 6246–6251, Curtis et al Isolation & Characterization of Thrombin–Activated Human Factor VIII.

Curtis et al Am. Soc. Hemat. (ASH) #1457 (HbSt) Dec. 1992.

Fay et al J. Biol. Chem. vol. 266 No. 14 (May 1991) pp. 8857–8862.

Fay et al J. Biol. Chem. vol. 267, No. 19 (Jul. 1992) pp. 13246–13250.

5,576,291

ACTIVATED FACTOR VIII AS A THERAPEUTIC AGENT AND METHOD OF TREATING FACTOR VIII DEFICIENCY

TECHNICAL FIELD OF THE INVENTION

This invention relates to a method of using activated Factor VIII as a therapeutic agent for patients having a deficiency of Factor VIII available for producing hemostasis. The invention also relates to a therapeutic composition containing activated Factor VIII.

Background

Hemophilia A is an X chromosome-linked congenital disorder caused by the lack of the biologically active coagulation protein Factor VIII. This congenital deficiency has been successfully treated by infusions of Factor VIII concentrate preparations isolated and purified from either blood plasma of donors having normal levels of Factor VIII, or cell cultures genetically engineered to express the Factor VIII coagulant protein. While this replacement therapy is effective in controlling bleeding episodes caused by the Factor VIII congenital disorder, approximately 15% of the hemophilia A patients treated in this manner develop inhibitors to Factor VIII after repeated infusions with Factor VIII concentrates. Patients who develop Factor VIII inhibitors, hereinafter inhibitor patients, become resistant to ordinary Factor VIII replacement therapy in varying degrees depending upon the quantity of inhibitors which are present in the patient's blood. Development of an inhibitor is suspected when the bleeding episode fails to respond to a previously adequate dose of Factor VIII concentrate. Inhibitors are currently believed to be antibodies which bind to the Factor VIII and diminish or destroy hemostatic function. Inhibitors to Factor VIII have also been observed in non-hemophiliacs who have normal levels of Factor VIII in their blood, although the incidence is far less common than in hemophiliacs.

Patients with Factor VIII inhibitors are treated to correct hemostasis by a number of therapeutic approaches but these have generally been less than fully satisfactory. Prothrombin complex concentrates and their activated forms have been shown to be effective in treating some Factor VIII inhibitor patients, but allergic and thrombogenic responses have been reported. Activated coagulation factors not present in a complex of Factors II, VII, IX and X such as activated Factor VII; activated Factor X combined with phospholipids; and human recombinant tissue factor are currently being evaluated as other means for treatment of inhibitor patients.

Most hemophiliacs with low levels of Factor VIII inhibitors have been successfully treated with larger quantities of Factor VIII concentrate preparations at dosages generally higher than those given to hemophiliacs without Factor VIII inhibitors. The use of larger amounts of Factor VIII for hemophiliacs with high levels of inhibitor has not been as successful. Repeated infusion of Factor VIII concentrates with or without activated prothrombin complex over a lengthy period of time has been shown to suppress completely the inhibitor in some patients. Because of the amount of Factor VIII concentrate required to suppress the inhibitor, this mode of treatment is very expensive.

Factor VIII proteins from different species, such as porcine Factor VIII, have also been used and are well tolerated by some inhibitor patients. Like the human Factor VIII concentrates, allergic and anamnestic reactions, however, have been reported with their usage, and as a result usually limits the use of the non-human Factor VIII to a very few administrations per patient. Once the antibodies for the non-human Factor VIII have developed, its subsequent administration is contraindicated.

Suppression or eradication of the inhibitor by use of immuno suppressive drugs such as corticosteroids, cyclophosphamide alone or in combination with Factor VIII or intravenous immune gamma globulin (IgG) have also been attempted. Combination therapy including the immuno suppressive drugs, Factor VIII and IgG together have been shown to be more effective than use of individual agents alone.

Treatment by administering polypeptide fragments of the Factor VIII coagulant protein, which are capable of binding to the patient's inhibitor antibodies thereby neutralizing its inhibitory effects, has also been proposed.

Recently, a method for preparing a stable activated form of human Factor VIII has been developed and disclosed in copending U.S. patent application Ser. No. 08/96332 filed Jul. 23, 1993, now abandoned method for preparing a stable activated porcine Factor VIII has been reported by Lollar et at., Biochemistry, 28:666 to 674, 1989.

SUMMARY OF THE INVENTION

The present invention relates to a method of treating a patient having a deficiency of Factor VIII available to produce hemostasis, with a therapeutically effective amount of stabilized activated Factor VIII to produce a hemostatic condition in said patient. The present invention further relates to a method for using stabilized activated Factor VIII to treat Factor VIII inhibitor patients. The invention also relates to therapeutic compositions comprising stabilized activated Factor VIII and a therapeutically acceptable adjuvant.

The activated Factor VIII protein used in this invention is an intact, non-fragmented, activated, mainly heterotrimer molecule. A method of preparing an activated human Factor VIII is described in U.S. patent application No. 08/96,332 filed Jul. 23, 1993. The method comprises activating human Factor VIII with a suitable activating agent, inactivating or removing the activating agent from the presence of the activated Factor VIII, maintaining the concentration of the activated human Factor VIII at a stabilizing level, and adjusting if necessary the pH of the activated Factor VIII to a mildly acidic state.

The term activated or activation refers to the conversion of the Factor VIII protein molecule into a form or forms in which it participates directly in the intrinsic clotting cascade which controls and stops bleeding.

The term hemophiliac refers to a person having a deficiency of Factor VIII in his blood. A person with average amounts of Factor VIII in his blood but accompanied by Factor VIII inhibitors is a non-hemophiliac with a bleeding disorder.

Herein, the term human Factor VIII denotes a functional protein capable of in vivo or in vitro correction of human Factor VIII deficiencies characterized, for example, by hemophilia A. Factor VIII includes the Factor VIII sequence shown in "Structure of Human Factor VIII", *Nature* 3 12: 339, FIG. 3. Thrombin fragmentation of the Factor VIII molecule is illustrated by a line diagram in "Structure of Human Factor VIII", *Nature* 312: 341, FIG. 6, or by a block diagram in "Genetic Engineering of Factor VIII", *Nature* 342: 207, FIG. 1.

DETAILED DESCRIPTION OF THE INVENTION

The present invention comprises a method for treating patients with stabilized activated Factor VIII who have a deficiency of Factor VIII available to produce hemostasis. This includes both patients with insufficient Factor VIII in their blood to produce the desired hemostatic effect, as well as those who have Factor VIII inhibitors in their blood which reduce the amount of Factor VIII available to produce hemostasis. Factor VIII inhibitors are believed to be antibodies which interact with either Factor VIII, activated Factor VIII, or both, to prevent their reaction and subsequent participation in the clotting cascade. There may also be inhibitors which are not antibodies, but are instead other chemical or biochemical moieties which interfere with the clotting action of Factor VIII.

The activated Factor VIII composition of this invention is useful in treating hemophilia A patients, and may be particularly useful with inhibitor patients because of the ability of activated Factor VIII to bypass some of the inhibitors and be used exclusively to produce the desired hemostatic effect. It is known that one way in which the Factor VIII inhibitors interfere with Factor VIII's hemostatic action is by preventing the activation of Factor VIII by thrombin when the Factor VIII is bound to von Willebrand factor. The infusion of pre-activated Factor VIII can bypass this inhibitory effect.

The activated Factor VIII is also useful in treating patients where the activated Factor VIII either partially or wholly overcomes or inactivates the Factor VIII inhibitors as well as producing the hemostatic effect. Patients with Factor VIII inhibitors have often been treated with large amounts of Factor VIII, which first overcome the inhibitors by binding to them, thereby eliminating that antibody-bound Factor VIII from availability as a hemostatic agent, but permitting the excess unbound Factor VIII to function in a hemostasis-producing manner. This method of treatment, using sufficient Factor VIII both to overcome the inhibitor and to produce hemostasis, has usually been expensive because of the large amounts of Factor VIII required, and has been occasionally time consuming as physicians increased the dosage in incremental steps to reach the point where bleeding is controlled.

The treatment and mode of administration useful in the practice of this invention can be similar to that followed in the administration of the unactivated form of Factor VIII. The activated Factor VIII can be lyophilized and stored in containers for a period of weeks or months, and subsequently reconstituted with sterile water into a solution for injection. It is also possible to activate the Factor VIII in a receptacle suitable for administering it to a patient, optionally perform stabilizing procedures, and then administer the activated Factor VIII to the patient without the intermediate steps of lyophilization and reconstitution into a solution.

The amounts of activated Factor VIII to be administered to a patient will vary widely, depending upon the nature of the bleeding episode, the presence or absence of Factor VIII inhibitors, the amount of Factor VIII naturally present in the patient's blood, and other factors. Dosage rates can range from 50 units of activated Factor VIII per kilogram of body weight or less up to 15,000 units or more per kilogram, and even greater than 250,000 units per kg. In most instances, it will be advisable to follow a general guideline, such as 500 units per kilogram, and adjust the guideline quantity for the individual patient to such a level that a hemostatic effect is achieved. The activity of activated Factor VIII is measured in units which correspond to the International Units, I.U., of activity for the unactivated coagulant Factor VIII.

Also included and useful in the practice of this invention are the structurally and therapeutically similar activated mammalian Factor VIII compositions other than human Factor VIII, such as porcine and bovine Factor VIII. Porcine Factor VIII has been used in humans to produce hemostasis, and the activated form may be similarly capable of producing hemostasis in humans. Porcine Factor VIII compositions can be prepared by the procedure in Lollar et al., *Biochemistry*, 28:666 to 674, 1989, as well as by other procedures described in the art.

The activated Factor VIII compositions useful herein can be prepared from any purified Factor VIII protein which can be converted to an active heterotrimer form containing the A1, A2, and A3-C1-C2 domains of Factor VIII as subunits. The subunits have molecular weights of about 50 kD for the A1, about 43 kD for the A2, and 73 kD for the A3-C1-C2. The starting human Factor VIII protein is typically derived from human plasma or from cell culture material containing functional Factor VIII protein.

One type of Factor VIII useful herein is the recombinant human protein generated in cell culture using genetically modified cells. Methods for expressing functional human Factor VIII in cell culture are known and described in U.S. Pat. Nos. 4,868,112; 4,757,006; and 4,965,199. The foregoing publications show examples of expressed human Factor VIII and variant forms of human Factor VIII which can be used in this invention.

The stabilized activated Factor VIII useful herein includes the activated human Factor VIII described in copending U.S. patent application Ser. No. 08/96332, filed Jul. 23, 1993, now abandoned. The activated Factor VIII compositions useful herein have customarily had coagulant Factor VIII specific activities greater than 50,000 units per milligram of protein and preferably greater than 100,000 units per milligram of protein, and even greater than 200,000 units/mg, and potencies greater than 15,000 coagulant Factor VIII units per milliliter of solution and even greater than 200,000 units per ml. These levels of specific activity and potency have been attained using a highly pure recombinantly produced Factor VIII. Activated Factor VIII prepared from plasma-derived Factor VIII is also useful herein, although its specific activity and potency upon activation may be less than the figures set forth above, because of the lower purity and concentration of the starting material for activation, when compared to the recombinantly produced Factor VIII. Multi-stage purifications, or purifications using longer immunoaffinity or affinity columns, thereby increasing the exposure of the Factor VIII to adsorbents, can be used to produce plasma-derived Factor VIII having purifies approaching that of the recombinant Factor VIII.

Methods for purifying the native human Factor VIII from plasma or from cell culture-derived human Factor VIII are also described in the prior art. The literature reciting the various methods for expressing functional human Factor VIII in cell culture material also illustrate the methods used for purifying the expressed human Factor VIII molecule. Additionally, a variety of methods are known for isolating and purifying human Factor VIII which may be used as starting material in the practice of this invention (U.S. Pat. No. 4,965,199; U.S. Pat. Redesign No. 32,011; U.S. Pat. Nos. 4,495,175; 4,758,657; 4,508,709; and 4,981,951).

Protein stabilizers can be added to the activated Factor VIII to reduce or eliminate the formation of degradation products from the desired activated Factor VIII product. Examples of stabilizers include albumin, sucrose, maltose, glycine, and trehalose. If protein stabilizers are used in the compositions, the specific activity of the compositions is calculated by determining the total protein content less the amount of added protein stabilizer if any remains in the composition. Following preparation and stabilization of the activated Factor VIII, the protein can be lyophilized and stored at reduced temperatures until the protein is to be administered, at which time it can be redissolved in sterile solution for administration.

One of the principal features of this invention is the therapeutic use of highly active Factor VIII in a concentrated and stabilized form. Stability for purposes of this invention means an activated Factor VIII which retains a level of its activity long enough to be administered to patients and produce a hemostatic effect. Depending upon the means of Factor VIII activation, stability of activated Factor VIII capable of producing a hemostatic effect can be as short as several seconds if the activated Factor VIII is formed in a receptacle such as a hypodermic syringe, or is formed immediately upon ejection from such a receptacle prior to or during injection into a patient. Activation produced in this manner can eliminate the need for subsequent actions designed to promote long time stability, such as lyophilization and low temperature storage, pH adjustment and the like. Also included within the scope of this invention are stabilized activated Factor VIII preparations which are stable for several weeks, thereby permitting the packaging of the activated Factor VIII for administration at a later date.

Stability is also measured in terms of the percentage of specific activity retained over a period of time. Preferred compositions retain at least 50%, and preferably at least 80%, of their specific activity for at least one month, preferably at least one year, following their activation.

The stability of activated Factor VIII is influenced by a number of conditions. The stability of the purified activated Factor VIII can be enhanced by achieving a certain minimum concentration of the activated Factor VIII in solution. To achieve the additional stability of the protein through concentration in solution, the activated Factor VIII should be at least 0.1 micromolar, preferably at least 0.2, and even more preferably at least 1.0 micromolar. A 1.0 micromolar solution has a potency of about 15,000 units per ml or greater. Under other processing conditions, the concentration of the activated Factor VIII can vary from the above guidelines.

Other conditions affecting stability are the pH of the final activated solution, the absence of an active activating agent, a low concentration of multivalent cations and the conditions of storage. The pH of the solution should be adjusted and kept at a mildly acidic condition, preferably at a pH between about 4 and 6.5, and more preferably between about 4.5 and 6.0. The multivalent cations should preferably be present at a maximum concentration of about 20 millimolar and more preferably at least 5 millimolar. Representative cations are calcium, other alkali earth metals, and transition metals such as iron, chromium, copper, zinc, manganese and the like.

Temperature of storage and exposure to UV radiation are two external conditions which can be controlled to maintain activity of the activated Factor VIII preparations. Generally, temperatures of 25° C. or less and UV exposure minimized by enclosure in an opaque container such as a box are preferred. Lyophilization following activation, optionally followed by storage at a reduced temperature, such as −80° C., is also effective in producing a stable activated Factor VIII preparation for long term storage.

If the activated Factor VIII solution is to be used for human or animal administration, the solution can be filtered through a sterilizing filter to remove microorganisms. The term "sterilizing filter" refers to a membrane device with pore sizes averaging 0.2 micron in diameter, which will retain bacteria and larger microorganisms while allowing the activated human Factor VIII solution to pass through. A more porous filter may be used if the activated solution is intended as a laboratory reagent for diagnostic or research use. The more porous filters are filter membrane devices with pore sizes typically of 0.45 or 0.5 micron diameter or larger.

The present invention also includes therapeutic compositions comprising a stabilized activated Factor VIII and a therapeutically acceptable adjuvant. The therapeutic composition can exist in the lyophilized state as well as in solution which is ready for administration to patients. The therapeutically acceptable adjuvant can be the materials dissolved in the buffer solution and the wash solutions before lyophilization and associated with the stabilized activated Factor VIII protein in the lyophilized state. Upon redissolving the lyophilizate, the adjuvants are redissolved in the solvent, which is usually sterile water specifically treated for injection.

The adjuvants include all of the components of the buffer solution used in the purification and isolation of the activated Factor VIII such as the sodium and calcium chloride, sodium acetate, Tris chloride, Hepes buffer, stabilizers, detergents, and other substances described herein and in copending U.S. patent application Ser. No. 08/96332, filed Jul. 23, 1993, now abandoned. The wash solutions referred to above are the solutions used in the immunoaffinity and affinity purification steps which can be used to purify Factor VIII, and include not only the washing solutions used to cleanse the columns holding the antibody coupled resins and ion-exchange columns, but also the eluting solutions used to extract the activated Factor VIII from the columns.

EXAMPLE 1

Human recombinant Factor VIII, obtained from Baxter Healthcare Corporation (Glendale, Calif.), was dissolved in a buffer solution consisting of 0.4M NaCl, 20 mM Tris-Cl, 5 mM $CaCl_2$, and 0.01% v/v Tween-20 pH 7.4, at a concentration of 0.4 mg Factor VIII per ml. The Factor VIII was then dialyzed into 0.15M NaCl, 20 mM Hepes, 5 mM $CaCl_2$, pH 7.4 overnight at 4° C. The dialyzed Factor VIII was stored at −20° C. until use. Factor VIII (31 nmole) was activated by digestion with human thrombin (1 nmole) for 10 minutes at 37° C. Activation was stopped by addition of 10 ml of 100 mM sodium acetate buffer adjusted to pH 5.5. Optionally, a 0.025 ml aliquot of the thrombin inhibitor PPACK (3 nmole) can be added just prior to the addition of the 100 mM sodium acetate. The sample was then loaded onto a CM-Sepharose column at 2 ml/min using a 50 ml superloop (FPLC Chromatography System, Pharmacia, Piscataway, N.J.). The column was pre-equilibrated with Buffer A (25 mM sodium acetate, 100 mM NaCl, 5 mM $CaCl_2$, 0.01% v/v Tween-20, pH 5.5). The sample was eluted from the column using a linear salt gradient from 0.1M NaCl in Buffer A to 1.0M NaCl in Buffer B (25 mM sodium acetate, 1.0M NaCl, 5 mM $CaCl_2$, 0.01% v/v Tween-20, pH 5.5). The gradient was run from 0 to 100% Buffer B in 60 minutes at a flow rate of 0.5 ml/min and the eluted peaks were detected by absorbance at 280 nm. The fraction containing activated Factor VIII eluted between 40 and 60% Buffer B. The activated Factor VIII was collected and stored at −80° C. The coagulant activity of activated human Factor VIII was measured in an in vitro modified one-stage coagulation assay using activated partial thromboplastin (APTI: Organon Teknika, Durham, N.C.) and commercially available Factor VIII deficient plasma (F8DP: George King Biomedical, Overland Park, Kans.). Standard curves were generated using normal pooled plasma control (FACT: George King Biomedial, Overland Park, Kans.). A quantity of 100 microliters of APTT was added to 100 microliters of F8DP and the VIII at 40 u/kg and later with activated Factor VIII at 400 u/kg. The results are set forth in Table 1, and show that both dosages of activated human Factor VIII shortened the cuticle bleeding time of hemophilic dogs, for the 5 hour period of observation following infusion.

TABLE 1

The in vivo efficacy of human activated Factor VIII in hemophilic dogs is reported here. Activated Factor VIII was infused, at either 40 or 400 units/kg, into hemophilic dogs (both moderate and severe hemophiliacs) and the cuticle bleeding time was determined at 0.5, 1, 3, and 5 hours post infusion. Activated Factor VIII was prepared using CM-Sepharose chromatography prepared according to Example 1 and had a specific activity greater than 130,000 units/mg (>30,000 units/ml).

| | Dog Number | | | |
|---|---|---|---|---|
| Time | 7095-S | 9048-M | 1011-S | 8046-M |
| | Activated Factor VIII: 40 units/kg | | | |
| Pre- | >12:00 min | 2:00 min | 11:00 min | 11:00 min |
| 0.5 | >12:00 min | 8:00 min | 2:50 min | 2:45 min |
| 1 | 9:30 min | 2:30 min | 11:50 min | >12:00 min |
| 3 | 8:00 min | >12:00 min | 6:00 min | 11:00 min |
| 5 | >12:00 min | ND | 4:30 min | 5:30 min |
| Comments | RT | RT | RT | RT |
| | Activated Factor VIII: 400 units/kg | | | |
| Pre- | 7:00 min | 8:00 min | >12:00 min | >12:00 min |
| 0.5 | >12:00 min | 4:45 min | 10:30 min | 3:55 min |
| 1 | 6:30 min | 4:45 min | >12:00 min | 2:50 min |
| 3 | >12:00 min | 5:00 min | 2:30 min | 3:30 min |
| 5 | 6:10 min | 3:20 min | 2:40 min | 3:00 min |
| Comments | RT | NT | NT | NT |

ND: Not Done
RT: Required Treatment (cryoprecipitate)
NT: Not Treated with cryoprecipitate
Subscript Legend:
"-S"; severe hemophiliacs
"-M"; moderate hemophiliacs mixture incubated for five minutes at 37° C. The clot time was measured from the addition of calcium to the formation of the first visible fibrin polymers. Standard curves were constructed using several dilutions of FACT (1, ⅓, ⅙, ¹⁄₂₁ units/ml) and plotting the observed clot times versus dilution on a log—log scale. One unit of activated Factor VIII was defined as the amount of material which gives a clot time of 55 to 60 seconds. To determine the specific activity reported in units of Factor VIII per milligram of protein, the coagulant activity (in units/ml) obtained above is divided by the concentration of total protein in solution. In this example, the total protein is all activated Factor VIII. The amount of activated Factor VIII protein is determined from the absorbance at 280 nanometers using the extinction coefficient at 280 nanometers of activated Factor VIII which has been determined to be 1.60 ml/mg cm. The concentration is determined using Beer's Law: $C = A \times e^{-1} \times L^{-1}$ (C, concentration in mg/ml; A, absorbance at 280 nanometers; e, extinction coefficient at 280 nanometers; and L, pathlength in centimeters). The activated human Factor VIII had a potency of 30,000 units/ml and a specific activity of 130,000 units/mg.

EXAMPLE 2

This example was carried out to measure the efficacy of the activated Factor VIII in vivo over a period of time. Four hemophilic dogs were infused, first with activated Factor

EXAMPLE 3

This example was carried out to determine whether activated Factor VIII has any adverse effect on normal hemostasis, such as initiating the blood clotting cascade with detrimental physiological results. A quantity of 100 rats were infused with one of the following solutions: buffer used with the activated Factor VIII, unactivated human Factor VIII, and activated human Factor VIII at final concentrations of 1, 10, and 100 units/mi. The dosage was approximately 6, 60, and 600 units per kg body weight, respectively. All of the rats survived the 24-hour observation period.

A single rat was subsequently infused with increasing doses of activated human Factor VIII. The final dosage concentration was 4400 u/ml (266,000 u/kg). Some post-ventricular contractions were detected upon dosages greater than 1000 u/ml, but the contractions were not fatal.

Based on the above two evaluations, activated Factor VIII is not considered toxic in rats at the dosages used.

EXAMPLE 4

The following experiment was performed to determine the in vitro efficacy of activated Factor VIII in human plasmas containing anti-Factor VIII inhibitors. Seven different inhibitor-containing plasmas were obtained from George King Biomedical (Overland Park, Kans.). The seven plasmas contained Factor VIII inhibitors at different levels of inhibitor activity, as indicated by the different levels of Bethesda Units. A Bethesda Unit is a measure of Factor VIII inhibitor activity. Human recombinant Factor VIII was obtained from Baxter Healthcare, Hyland Division (4307 units/mg, 1736 units/ml), and activated human Factor VIII was prepared by CM-Sepharose chromatography as described in Example 1. The activated Factor VIII had a specific activity of 250,000 units/mg and a potency of 70,000 units/ml. The unactivated Factor VIII and the activated Factor VIII are added to the Factor VIII inhibitor plasmas to produce solutions at a concentration of 0.28 nanomolar.

The coagulation times were measured in the modified one-stage coagulation assay in the presence of equal molar quantities of either Factor VIII or activated Factor VIII. The results are shown in Table 2. In each of the plasmas tested, activated Factor VIII produced a shorter coagulation time compared to the same sample with unactivated Factor VIII. The average difference in clotting times was 24.8 seconds. The shorter coagulation time for activated Factor VIII solutions shows that activated Factor VIII is more effective in producing clotting in Factor VIII inhibitor plasmas than is the unactivated protein.

TABLE 2

Coagulation Times for Factor VIII-Inhibited Plasmas.

| Bethesda Units | Unactivated Factor VIII | Activated Factor VIII |
| --- | --- | --- |
| 8 | 50.2 sec. | 30.1 sec. |
| 20 | 57.4 sec. | 34.3 sec. |
| 128 | 67.0 sec. | 38.7 sec. |
| 140 | 72.0 sec. | 44.7 sec. |
| 192 | 74.5 sec. | 48.2 sec. |
| 342 | 78.1 sec. | 53.3 sec. |
| 380 | 87.3 sec. | 62.0 sec. |

EXAMPLE 5

The following experiments were performed to determine the in vitro inhibition by anti-Factor VIII inhibitors of either Factor VIII or activated Factor VIII. The assay used was based on Factor X activation by an enzymatic complex consisting of Factor IXa, phospholipid, calcium, and limiting amounts of Factor VIIIa. Assay kits were purchased from Baxter Healthcare, Dade Division (Miami, Fla.). Whole antibody populations were purified from commercially available NPP, F8DP, and an inhibitor-containing plasma. The inhibitor-containing plasma had an inhibitor titer of 342 Bethesda Units (BU). Each antibody preparation was prepared by loading 1 ml of plasma onto a 3 ml Protein G column (Pharamacia, Piscataway, N.J.) which was pre-equilibrated with phosphate-buffered saline at pH 7.4. Immunoglobulins were eluted from the column by the addition of 0.1M glycine at pH 2.0. Following elution, the IgG containing fractions were immediately neutralized by the addition of 1 ml of 0.1M Hepes at pH 7.4. Samples were then dialyzed extensively into 0.1M Hepes at pH 7.4.

It was found that for a single antibody concentration over a range of either Factor VIII or activated Factor VIII concentrations (0.1 to 0.4 nM), the relative rate of Factor Xa production was two to three fold greater in the presence of activated Factor VIII compared to Factor VIII. In a second experiment, using equal molar concentrations of either Factor VIII or activated Factor VIII in the presence of decreasing amounts of inhibitory antibody, it was observed that maximum production of Factor Xa was reached at the 1 to 160 dilution of antibody in the presence of Factor VIII and the 1 to 40 dilution of antibody in the presence of activated Factor VIII.

These experiments show that the relative rate of Factor Xa production in the presence of a high Bethesda Unit titer of inhibitory antibodies is less inhibited with activated Factor VIII compared to Factor VIII, and that there are fewer inhibitory antibodies generated against activated Factor VIII compared to antibodies generated against Factor VIII.

What is claimed is:

1. A method of treating a patient having a deficiency of Factor VIII available to produce hemostasis with a therapeutically effective amount of stabilized, activated Factor VIII to produce a hemostatic condition in said patient.

2. A method according to claim 1 wherein said patient's deficiency is due to or accompanied by the presence of Factor VIII inhibitors in association with Factor VIII.

3. A method according to claim 2 wherein said Factor VIII inhibitors do not completely inhibit the hemostatic activity of the stabilized, activated Factor VIII.

4. A method according to claim 1 wherein said stabilized, activated Factor VIII is used to bypass Factor VIII inhibitors and produce a hemostatic condition in said patient.

5. A method according to claim 4 wherein said therapeutically effective amount of stabilized, activated Factor VIII is from about 1000 to about 5000 units per kilogram of body weight.

6. A method according to claim 1 wherein said therapeutically effective amount of stabilized, activated Factor VIII is equivalent to from about 50 to about 250,000 units of coagulant Factor VIII per kilogram of body weight.

7. A method according to claim 1 wherein said therapeutically effective amount of stabilized, activated Factor VIII is equivalent to from about 50 to about 15,000 units of coagulant Factor VIII per kilogram of body weight.

8. A method according to claim 7, wherein said stabilized, activated Factor VIII has a specific activity greater than 100,000 units per milligram of protein.

9. A method according to claim 1 wherein said stabilized, activated Factor VIII has a specific activity greater than 50,000 units per milligram of protein.

10. A method according to claim 1 wherein said stabilized, and activated Factor VIII has a potency greater than 15,000 units per milliliter of solution.

11. A method according to claim 1 wherein said stabilized, activated Factor VIII is formed and subsequently injected into said patient without performing further stabilizing procedures.

12. A method according to claim 1 wherein said patient is a hemophiliac with Factor VIII inhibitors.

13. A method according to claim 1 wherein said patient is a hemophiliac without Factor VIII inhibitors.

14. A method according to claim 1 wherein said patient is a non-hemophiliac with Factor VIII inhibitors.

15. A therapeutic composition comprising a stabilized, activated Factor VIII and a therapeutically acceptable adjuvant.

16. A composition according to claim 15 wherein said composition is in the form of a lyophilized material.

17. A composition according to claim 15 wherein said composition is in the form of a solution suitable for administration to a patient.

18. A composition according to claim 15 wherein said adjuvant comprises the materials present in buffer solutions and wash solutions used for purification and isolation of the stabilized, activated Factor VIII.

19. A composition according to claim 15 wherein said stabilized, activated Factor VIII has a specific activity greater than 50,000 units per milligram of protein.

20. A composition according to claim 15 wherein said stabilized, activated Factor VIII has a potency greater than 15,000 units per milliliter of solution.

* * * * *